United States Patent [19]

Simko

[11] Patent Number: 4,690,820
[45] Date of Patent: Sep. 1, 1987

[54] HIGH-CALORIC, HIGH-FAT DIETARY FORMULA

[75] Inventor: Vlado Simko, Staten Island, N.Y.

[73] Assignee: The State University of New York, Albany, N.Y.

[21] Appl. No.: 742,299

[22] Filed: Jun. 7, 1985

[51] Int. Cl.$^4$ .................... A61K 33/42; A61K 33/30; A61K 33/06; A61K 31/00
[52] U.S. Cl. .................................. 424/128; 424/145; 424/154; 514/2; 514/23; 514/552; 514/52; 514/814; 514/878; 514/893; 514/904
[58] Field of Search .................. 424/145, 128, 154; 514/78, 552, 2, 21, 23, 53, 54, 60, 773, 775, 778, 777, 814, 878, 893, 504

[56] References Cited

FOREIGN PATENT DOCUMENTS 2520606 7/1976 Fed. Rep. of Germany .

OTHER PUBLICATIONS

Physicians Desk Reference, 31 Ed. Nutri-1000 p. 1577, 1977.
Physicians' Desk Ref. 30th Ed., 1976 pp. 780, 1021–1024, 1032–1033 and 1327.
AMA Drug Evaluations, 4th Ed. 1982 pp. 856–857.
Handbook Non Prescription Drugs 6th Ed. pp. 206–207.
C. A. 91:73478 1979.

Primary Examiner—Johnnie R. Brown
Assistant Examiner—John W. Rollins, Jr.
Attorney, Agent, or Firm—Omri M. Behr

[57] ABSTRACT

A high caloric, high fat dietary composition having greater than 2.5 Kcals/ml. is utilizable for enteral hyperalimentation in severe malnutrition. The composition has an increased proportion of fat which gives it a higher caloric density and enables a patient to be fed up to 6000 Kcals/24 hour period.

10 Claims, No Drawings

HIGH-CALORIC, HIGH-FAT DIETARY FORMULA

BACKGROUND OF THE INVENTION

Critically ill patients often lose their ability to ingest normal amounts of food necessary to maintain adequate nutritional levels. Typical of such patients are those having various oroesophageal cancers, strokes, neuromuscular dystrophy and Parkinson's Disease. Many cancer therapy routines require periods of abstinence. Other cancer therapies often cause nausea and vomiting which result in the interruption of a patient's normal eating habits. Obviously, such patients become malnourished and resort must be had to some form of hyperalimentation in order to sustain the patient. Enteral hyperalimentation is usually the treatment of choice since it produces fewer side effects than the introduction of nutrients directly into a vein.

The compositions presently marketed as complete therapeutic diets for enteral hyperalimentation all contain 2 Kcal/ml or less. These products have a low fat and high carbohydrate content. Carbohydrates are osmotically more active than fats. Low fat diets have a higher osmolality which frequently leads to diarrhea. This reduces the feeding load of such products to less than 3500 Kcal/24 hours. Also, the lower caloric density of low fat diets precludes higher intake because of the volume limitations. Although central vein hyperalimentation can provide more energy and nutrients, this mode of feeding has frequent serious side effects which limit the intake to below 4000 Kcal/24 hours.

Compositions which would provide a higher caloric intake via enteral hyperalimentation without side effects would obviously be desirable. Heretofore, such compositions have been unknown. Low fat content of the presently available diets is based on the observation of increased stool fat in malabsorption. (See Davis-Christopher Textbook of Surgery, Ed. D. C. Sabiston, Jr., W. B. Saunders Co., Philadelphia, Pa., (1977) p. 1021; Clinics In Gastroenterology, 8, 373 (1979); Gastrointestinal Disease, II, 2nd. Ed., W. B. Saunders Co., Philadelphia, Pa., (1978), "The Short Bowel Syndrome", Trier, 1137). This accepted clinical judgment completely neglects that with increasing intake of dietary fat there is a linear increase in the absorption of fat. A great example from the nature the very high fat content of breast milk provided for the first weeks of life has not been conceptually considered in the development of routinely available diets.

SUMMARY OF THE INVENTION

The compositions of the present invention is a high caloric, high fat dietary composition having 2.5–3.6 Kcal/ml and deriving 45–75% of its calories from fat. This composition comprises:
- 120–325 gms/liter fat;
- 56–69 gms/liter protein; and
- 168–207 gms/liter carbohydrate.

It additionally may contain such vitamins and minerals in amounts sufficient to fulfull the adult recommended daily allowances when approximately 1 to 2 liters of the composition are ingested in a 24 hour period. The comppposition is thus a nutritionally complete dietary composition capable of use in seriously ill patients without side effects. Its high Kcal/ml enables the patients to be fed a lower volume while the higher percentage of fat provides better patient tolerance and a lower incidence of side effects.

DESCRIPTION OF THE PREFERRED EMBODIMENTS

The high caloric, high fat dietary composition of the present invention is prepared by conventional techniques for such dietary compositions.

Non-fat sources for this new high caloric, high fat diet can be obtained in a liquid form from several commercial manufacturers. When appropriately mixed with dietary fat, these sources contain protein, carbohydrates, vitamins, minerals and trace metals at a level consistent with the Recommended Daily Allowances. These commercial products can be obtained in fixed compositions or as individual nutrients. When adding the fat component, appropriate mixing and adequate use of emulsifying agents has to be made to assure a physically stable composition.

A variety of emulsifiers can be used to assure a stable lipid emulsion. From our experiments with different lipophilic and hydrophilic surfactants (phospholipids, carrageenan and tweens), we obtained best results with a commercial mixture of mono- and diglycerides at the level of 1 to 5 percent of total fat.

Using a laboratory or a commercial homogenizer, the dietary fat is vigorously blenderized with the remaining components of the diet for about 20 min at 15,000 to 22,000 rpm of the rotor.

Microscopic studies of the stability of this composition showed no changes in the consistency of the emulsion when aliquots of a typical diet sample, stored at 4 Celsius, were examined every two weeks for a total of 36 weeks.

The fat portion of the composition may be contributed by either an animal or vegetable source. Although animal fats such as lard or butter have essentially equal caloric and nutritional values and can be used, vegetable oils are highly preferred in the practice of the present invention due to their ready availability, ease of formulation, absence of cholesterol and lower concentration of saturated fatty acids. Typical vegetable oils suitable for use in the composition of the present invention are those such as corn oil, sunflower oil and soybean oil. Partially hydrogenated fats may also be utilized.

Where the patient to be treated has a compromised digestive/absorptive function, the digestion of fat can be improved by additionally including in the fat portion of the composition of the present invention, a small proportion of dietary fat in the form of medium-chain triglyceride, e.g., fractionated peanut oil. Absorption studies in patients with compromised bowel function showed excellent effect when medium-chain triglycerides represented 20 to 75 g. of the daily fat intake.

The protein portion of the dietary composition of the present invention is typically a balanced source of essential and non-essential amino acids such as calcium and sodium caseinate or egg white solid. Although free amino acids may also be used, partially hydrolyzed proteins (soy, meat or whey) or a complete protein such as soy protein isolate are preferable.

The carbohydrate portion of the dietary composition of the present invention is a blend of simple and complex carbohydrates. Suitable for use are glucose, fructose, sucrose, corn syrup, malt, maltose, isomaltose, partially hydrolyzed corn starch, malodextrins, glucose oligo/and polysaccharides.

The dietary compositions of the present invention also contain the recommended daily allowance of vitamins and minerals for adults so that they provide complete nutrition for a patient. Typically, vitamins A, B6, B12, C, D, E and K and thiamine, riboflavin, niacin, calcium, phosphorus, magnesium and zinc are included in the composition. The amounts included in the composition are such that the adult recommended daily allowances of each will be provided upon ingestion of 1-2 liters of the dietary composition.

Typically, the concentration of vitamins and minerals in the present composition will be somewhat lower than found in the prior art formulation of this type. This is because the present compositions are better tolerated by patients so that larger volumes of feeding are tolerated. The anticipated daily dose of approximately 1.5 liters of the present composition will thus provide more than the recommended allowances of each of the necessary vitamins and minerals. If it is anticipated that a lower volume of the present composition will be ingested by a given patient, the amounts of vitamins and minerals added to the composition can be adjusted in an appropriate manner so that the recommended daily allowances will be met.

The method of the present invention additionally comprises the feeding by enteral hyperalimentation using the compositions. Typically, the patient will be fed from one to two liters/24 hour period of the compositions of the present invention. This will generally provide 3500-6000 Kcal/24 hour period to the patient which will sustain the patient and, in most cases, even provide the patient with sufficient calories so as to afford a much desired weight gain.

EXAMPLE I

One liter of a very high caloric, high fat dietary composition is formulated using the following:

| | |
|---|---|
| 300 g | vegetable oil (Mazola Brand corn oil) |
| 700 g | non-lipid components: |
| 60 g | Protein (calcium caseinate, Casec) |
| 164 g | Carbohydrate (corn syrup, Karo) |
| 5000 units | Vitamin A |
| 400 units | Vitamin D |
| 60 units | Vitamin E |
| 300 mg | Vitamin C |
| 200 mcg | Vitamin K |
| 3 mg | Vitamin $B_1$ |
| 3 mg | Vitamin $B_2$ |
| 40 mg | Niacin |
| 3 mg | Vitamin $B_6$ |
| 12 mcg | Vitamin $B_{12}$ |
| 1 g | Calcium ion (as gluconate) |
| 1 g | Phosphorus ion (as phosphate) |
| 400 mg | Magnesium ion (as sulphate) |
| 15 mg | Zinc ion (as sulphate) |
| (water to 1000 ml) | |

This diet contains 3.6 Kcal/1 ml.

This diet is indicated for patients with limited tolerance of dietary volume, e.h., after major gastric or small intestinal resections.

EXAMPLE II

A high caloric, high fat dietary composition with 3.0 Kcal/ml is formulated using the following:

223 g vegetable oil (Mazola corn oil) mixed with 777 g non-lipid components and other nutrients as in Table 1.

This formula can be used for most patients requiring vigorous enteral hyperalimentation. We have extensively tested the tolerance, safety and nutritional response of this formula in metabolic clinical studies. The diet has a bland taste which can be improved by the addition of artificial flavorings.

This formula can also be conveniently used as a high-caloric supplement to a regular diet to improve the intake of nutrients, with only a minimum additional volume load. In order to achieve high caloric intakes the best way to administration is via a feeding tube, with continuous flow at 60-80 ml/hour.

EXAMPLE III

A high caloric, high fat dietary composition of 2.5 Kcal/ml is formulated using the following:

157 g vegetable oil mixed with 843 g non-lipid components, outlined in detail in Table 1. Vitamins, minerals and trace elements as for composition in Example I.

This diet is indicated for patients requiring enteral hyperalimentation who are at a risk of dehydration, e.g., patients with impaired renal function and azotemia.

Table 1 below compares three embodiments of the present invention with liquid dietary formulas presently available on the market. All of the formulas can be defined as nutritionally complete, i.e., 2000 ml. (2 liters) of the diet or less meet the recommended daily allowances of an adult for vitamins and minerals. As will be noted from the tables the three embodiments of the present invention differ substantially from the prior art formulas in that they have a high caloric density (greater than 2.4 Kcals/ml.), a high fat content (greater than 100 grams/liter) and a high proportion of calories derived from fat relative to total calories (greater than 45%).

TABLE 1

Nutritional Components of Diets

| DIET | | | |
|---|---|---|---|
| Examples of the Invention | | | |
| | High Cal 3.6 (Example I) | High Cal 3.0 (Example II) | High Cal 2.5 (Example III) |
| Kcal/ml. | 3.6 | 3.0 | 2.5 |
| Fat g/L | 300 | 223 | 157 |
| Fat % cal | 75 | 67 | 57 |
| Protein g/L | 56 | 63 | 69 |
| Carbohydrate g/L | 168 | 189 | 207 |
| Vitamin A IU/L | — | 2772 | — |
| Vitamin D IU/L | — | 227 | — |
| Vitamin E IU/L | — | 42 | — |
| Vitamin C mg/L | — | 170 | — |
| Vitamin K mg/L | — | 140 | — |

| | Commercial Products | | | | |
|---|---|---|---|---|---|
| | Magnacal (Organon) | Travasorb MCT (Travenol) | Isocal HCN (Mead Johnson) | Ensure Plus (Ross) | Vivonex HN (Norwich Eaton) |
| Kcal/ml. | 2 | 2 | 2 | 1.5 | 1 |
| Fat g/L | 80 | 66 | 91 | 53 | 0.87 |
| Fat % cal | 36 | 30 | 41 | 32 | 0.8 |
| Protein g/L | 70 | 98 | 75 | 55 | 42 |
| Carbohydrate g/L | 250 | 245 | 225 | 200 | 210 |
| Vit. A IU/L | 5000 | 5000 | 3000 | 2637 | 1667 |
| Vit. D IU/L* | 400 | 400 | 270 | 211 | 133 |
| Vit. E IU/L. | 60 | 60 | 50 | 48 | 10 |
| Vit. C IU/L | 300 | 300 | 200 | 160 | 20 |

-continued

| | Commercial Products | | | |
|---|---|---|---|---|
| | Magnacal (Organon) | Travasorb MCT (Travenol) | Isocal HCN (Mead Johnson) | Ensure Plus (Ross) | Vivonex HN (Norwich Eaton) |
| Vit. K IU/L | 210 | 1900 | 167 | 210 | 22 |

Note: Despite a higher proportion of fat, the high cal 3 Kcal/ml (Example II) has a normal kelogenic index and a normal nitrogen/calorie ratio of 1:300.

Safety of this diet and optimum composition for absorption was first validated in our rat studies, perfusing the whole small intestine in vivo with formula listed in Example III. Labeled trioleine was used as a marker for fat absorption. Best absorption was achieved with the addition of medium chain triglycerides to the fat.

Table 2 below gives the metabolic data obtained to illustrate the tolerance of a dietary composition of the present invention. The composition utilized in these experiments was identical to that shown above in Example II. In the experiments, a composition as described in Example II was fed to 10 patients for prolonged periods as the sole source of nutrition. The average caloric intake/24 hours obtained was 3899 Kcals/patient over 232 patients/day. No complications were reported during this extensive feeding study where patients were up to four weeks on this special diet, with intakes up to 8400 Kcal/day.

Specifically, there was no case of diarrhea, which confirms a very adequate absorption of nutrients provided in this diet. Fecal fat and fecal nitrogen in these 10 patients confirmed a very satisfactory absorption.

TABLE 2

Preliminary anthropometric and metabolic data in 10 severely malnourished patients[a] ingesting High Cal (3.0 Kcals/ml) as sole source of nutrition.

| | n | mean | 1 SEM | Range min | Range max |
|---|---|---|---|---|---|
| Males, age (yr) | 10 | 65.6 | 3.3 | 42 | 76 |
| Body wght, initial (kg) | 10 | 48.1 | 2.1 | 38.2 | 57.4 |
| Percent, initial, of ideal body wght/hght$^2$ | 9[b] | 60.5 | 2.6 | 47.7 | 70.6 |
| Days in study with HFD | 10 | 23.2 | 2.2 | 10 | 28 |
| Average intake Kcal/24 hr | 10 | 3899 | 368 | 2079 | 5029 |
| Maximum intake Kcal/24 hr | 10 | 5370 | 609 | 3000 | 8400 |
| Average diet intake, ml/24 hr | 10 | 1300 | 123 | 693 | 1736 |
| Maximum diet intake, ml/24 hr | 10 | 1790 | 203 | 1000 | 2800 |
| Wght gain, lb/24 hr[c] | 10 | 0.45[c] | 0.12 | 0[c] | 1.04 |
| Wght gain/feeding period[c] | 10 | 10.7[c] | 3.2 | 0[c] | 28.2 |

[a]Four oroesophageal cancers, 1 prostatic cancer with metastases, 1 liver cirrhosis with lung TB, 2 debilitated patients after strokes, 1 neuromuscular dystrophy, 1 Parkinson's disease, severe.
[b]1 patient was a bilateral, above the knee amputee.
[c]Some patients initially had edema and ascites which they lost during refeeding. No patient developed edema or ascites in the experimental period.

I claim:

1. A high caloric, high fat dietary composition having 2.5/3.6 Kcals/ml. and deriving 45-75% of its calories from fat which comprises:
   120-325 grams/liter fat;
   56-69 grams/liter protein; and
   168-207 grams/liter carbohydrate.

2. A composition according to claim 1 having about 3.6 Kcals/ml. which comprises about:
   300 grams/liter fat;
   56 grams/liter protein; and
   168 grams/liter carbohydrate.

3. A composition according to claim 2 which further comprises vitamins A, B6, B12, C, D, E and K and thiamine, riboflavin, niacin, calcium, phosphorus, magnesium and zinc in their recommended daily allowances/1 to 2 liters of composition.

4. A composition according to claim having about 3.0 Kcals/ml. which comprises about:
   223 grams/liter fat;
   63 grams/liter protein; and
   189 grams/liter carbohydrate.

5. A composition according to claim 4 which further comprises vitamins A, B6, B12, C, D, E and K and thiamine, riboflavin, niacin, calcium, phosphorus, magnesium and zinc in their recommended daily allowances/1 to 2 liters of composition.

6. A composition according to claim 1 having about 2.5 Kcals/ml. which comprises about:
   157 grams/liter fat;
   69 grams/liter protein; and
   207 grams/liter carbohydrate.

7. A composition according to claim 6 which further comprises vitamins A, B6, B12, C, D, E and K and thiamine, riboflavin, niacin, calcium, phosphorus, magnesium and zinc in their recommended daily allowances/1 to 2 liters of composition.

8. A composition according to claim 1 which further comprises vitamins A, B6, B12, C, D, E and K and thiamine, riboflavin, niacin, calcium, phosphorus, magnesium and zinc in their recommended daily allowances/1 to 2 liters of composition.

9. A method of enteral hyperalimentation which comprises administering to a patient in need of such therapy a caloric, high fat dietary composition having 2.5-3.6 Kcals/ml. and deriving 45-75% of its calories from fat which comprises:
   120-325 grams/liter fat;
   56-69 grams/liter protein; and
   168-207 grams/liter carbohydrate;
in an amount sufficient to provide 3500-6000 Kcals/24 hours.

10. A method according to claim 9 which further comprises the addition of the recommended daily allowances of vitamins A, B6, B12, C, D, E and K and thiamine, riboflavin, niacin, calcium, phosphorus, magnesium and zinc to the dietary composition.

* * * * *